(12) United States Patent
Wagner (10) Patent No.: US 12,290,623 B2
(45) Date of Patent: May 6, 2025

(54) AUTOMATIC PRIMING AND RINSING OF AN EXTRACORPOREAL BLOOD TREATMENT APPARATUS

(71) Applicant: B. Braun Avitum AG, Melsungen (DE)

(72) Inventor: André Wagner, Kassel (DE)

(73) Assignee: B. Braun Avitum AG, Melsungen (DE)

( * ) Notice: Subject to any disclaimer, the term of this patent is extended or adjusted under 35 U.S.C. 154(b) by 274 days.

(21) Appl. No.: 18/022,933

(22) PCT Filed: Aug. 24, 2021

(86) PCT No.: PCT/EP2021/073402
§ 371 (c)(1),
(2) Date: Feb. 23, 2023

(87) PCT Pub. No.: WO2022/048955
PCT Pub. Date: Mar. 10, 2022

(65) Prior Publication Data
US 2024/0009368 A1    Jan. 11, 2024

(30) Foreign Application Priority Data
Sep. 2, 2020 (DE) ...................... 10 2020 122 937.2

(51) Int. Cl.
*A61M 1/36* (2006.01)
(52) U.S. Cl.
CPC .................. *A61M 1/3649* (2014.02)
(58) Field of Classification Search
CPC .............. A61M 1/1682; A61M 1/3647; A61M 1/3649; A61M 1/365; A61M 2205/3331
See application file for complete search history.

(56) References Cited

U.S. PATENT DOCUMENTS 9,579,440 B2    2/2017    Hogard et al.

FOREIGN PATENT DOCUMENTS

| DE | 3442744 C2 | 7/1988 |
| EP | 1457218 A1 | 9/2004 |

(Continued)

OTHER PUBLICATIONS

Search Report received in German Application No. 10 2020 122 937.2 dated May 5, 2021, with translation, 10 pages.

(Continued)

*Primary Examiner* — Dirk R Bass
(74) *Attorney, Agent, or Firm* — Christopher A. Rothe; CM Law (57) ABSTRACT

An extracorporeal blood treatment device and method for priming and rinsing an extracorporeal blood treatment device. The extracorporeal blood treatment device includes an extracorporeal circuit, a dialyzer, and a dialyzing liquid circuit. The extracorporeal blood treatment device is configured for priming and rinsing the extracorporeal circuit, dialyzer and dialyzing liquid circuit. An arterial section and a venous section of the extracorporeal circuit are connected by a connector device. A control unit of the extracorporeal blood treatment device is configured to control the priming such that a liquid is supplied from the dialyzing liquid circuit via the dialyzer to the extracorporeal circuit and to control the rinsing such that it occurs via a created pressure difference between the extracorporeal circuit and the dialyzing liquid circuit for causing a liquid transfer via the dialyzer, in particular from the extracorporeal circuit to the dialyzing liquid circuit.

12 Claims, 2 Drawing Sheets

(56) References Cited

FOREIGN PATENT DOCUMENTS

| | | | |
|---|---|---|---|
| EP | 2361643 | B1 | 6/2016 |
| EP | 3127564 | B1 | 12/2018 |
| JP | 2001245970 | A | 9/2001 |
| JP | 2013248335 | A | 12/2013 |
| WO | 2013183599 | A1 | 12/2013 |

OTHER PUBLICATIONS

Search Report received in International Application No. PCT/EP2021/073402 dated Jan. 4, 2022, with translation, 5 pages.
Written Opinion received in International Application No. PCT/EP2021/073402 dated Jan. 4, 2022, with translation, 19 pages.

AUTOMATIC PRIMING AND RINSING OF AN EXTRACORPOREAL BLOOD TREATMENT APPARATUS

CROSS-REFERENCE TO RELATED APPLICATIONS

This application is the United States national stage entry of International Application No. PCT/EP2021/073402, filed Aug. 24, 2021, and claims priority to German Application No. 10 2020 122 937.2, filed Sep. 2, 2020. The contents of International Application No. PCT/EP2021/073402 and German Application No. 10 2020 122 937.2 are incorporated by reference herein in their entireties.

FIELD

The present disclosure relates to an extracorporeal blood treatment device, in particular a dialysis machine, which is prepared or, respectively, configured for automatic priming and rinsing thereof. Furthermore, the present disclosure relates to a method for automatically priming and rinsing an extracorporeal blood treatment device.

BACKGROUND

Extracorporeal (blood) circuits for carrying blood outside a patient's body during a blood purification process are known from practice. Such extracorporeal circuits are filled with a priming solution or, respectively, priming liquid before the start of a treatment. This filling of the extracorporeal circuit and a dialyzer with priming solution or, respectively, priming liquid (priming) serves as a preparation of the extracorporeal circuit and the dialyzer for the subsequent treatment. In particular, priming serves to displace air still present in the extracorporeal circuit and in the dialyzer prior to the treatment with a physiologically compatible liquid or solution in order to prevent this air from entering the patient's vascular system during and especially at the beginning of the blood treatment.

In addition to the priming or, respectively, priming process, for preparation of the extracorporeal circuit and the dialyzer for the subsequent treatment, usually a rinsing/flushing or, respectively, rinsing process of the extracorporeal circuit and of the dialyzer are performed. The rinsing or, respectively, rinsing process is usually performed simultaneously with or (immediately) subsequent to the priming or, respectively, priming process. The rinsing or, respectively, rinsing process serves in particular to flush residual substances/pyrogens out of the extracorporeal circuit and out of the dialyzer, in particular out of a membrane thereof (the pyrogens are membrane-permeable). Such residual substances/pyrogens may originate from a production, packaging or set-up process and represent a potential hazard to the patient.

When the dialyzer and a tubing system forming the extracorporeal (blood) circuit are prepared, that is, when the priming and rinsing thereof has been performed, the patient can principally be put on, and the priming or, respectively, rinsing liquid is drained from the completely filled system and replaced on one side by the patient's blood.

The present disclosure relates in particular to the preparation of the extracorporeal blood treatment device, i.e. the priming and rinsing. In other words, putting-on/a treatment (of) a patient is preferably not subject matter of the present disclosure, so that according to the disclosure preferably no contact of the extracorporeal blood treatment device with a patient is provided.

A priming/priming via an external saline bag is known from the prior art. Thereby, a saline bag is connected to a tube of the extracorporeal circuit (to one side of the blood tubing system) and the priming liquid is filled into the tubing system and the dialyzer. To suitably fill the dialyzer with liquid, it must be rotated in between to remove any remaining air bubbles from the system. The used liquid is thereby collected in an empty bag.

Furthermore, the so-called online priming is known from the prior art. In online priming, dialyzing liquid is provided by the blood treatment device and input to the blood tubing system and the dialyzer via a substitute connection with the aid of an arterial blood pump. Also in this priming process the dialyzer needs to be rotated to remove any remaining air bubbles from the system.

Both these aforementioned priming methods have the disadvantage that steps that principally have to be taken manually by a user are required, for example when rotating the dialyzer. Due to a high cost pressure and partly strict guidelines (e.g. from the Centers for Disease Control and Preventions in the United States), principally an automatic preparation of the extracorporeal blood treatment device (priming and rinsing) is desirable. Thereby, preferably no saline bag and no disposables, which have to be removed and disposed of before the therapy, should be used.

It is also known from the prior art that dialyzing liquid/dialysate (instead of a saline solution) is used for priming. Thereby, the dialyzing liquid is transported across a membrane of the dialyzer into the blood tubing system. If the arterial and venous blood tubing are thereby short-circuited, dialyzing liquid can be pumped from the dialyzing liquid side by means of a suitable pump actuation and by means of suitable valve positions into the dialyzer and the blood tubing system, and these can thus be filled. In this context, reference is made, for example, to EP 3 127 564 B1 or EP 1 457 218 A1.

Other automatic priming methods are known, for example, from U.S. Pat. No. 9,579,440 B2 or EP 2361 643 B1.

The state of the art has in particular the disadvantage that no suitable automatic rinsing processes exist which can rinse the extracorporeal circuit and the dialyzer in a satisfactory manner (for removal of the residual substances/pyrogens).

SUMMARY

Object of the present disclosure is to provide an improved automatic preparation (comprising both priming and rinsing) of an extracorporeal blood treatment device. In particular, both during the priming and during the rinsing of the dialyzer and of extracorporeal tubing system, a number of required disposables/disposable items is to be reduced, or, respectively, preferably few/no additional disposables/disposable items and no substitution connection ought to be required.

The present disclosure relates first to an extracorporeal blood treatment device with: an extracorporeal circuit comprising an arterial section and a venous section, a dialyzer, and a dialyzing liquid circuit, wherein: the extracorporeal circuit and the dialyzing liquid circuit are separated from each other by a membrane provided in the dialyzer; the extracorporeal blood treatment device is prepared or, respectively, configured for priming and rinsing (of) the extracorporeal circuit and the dialyzer prior to a first-time use of the extracorporeal circuit and (of) the dialyzer, and for this purpose the arterial section and the venous section are short-circuited or, respectively, connected via a connector device; the dialyzing liquid circuit has a dialyzer inlet valve, a dialyzer outlet valve and at least one flow pump; the extracorporeal circuit has at least one vent valve; and the extracorporeal blood treatment device further comprises a control unit which is configured to control the priming such that a liquid, in particular priming/rinsing/dialyzing liquid, is supplied from the dialyzing liquid circuit across the membrane of the dialyzer to the extracorporeal blood circuit. The control unit is further configured to control the rinsing of the extracorporeal blood treatment device, in particular of the dialyzer and the extracorporeal circuit, to be performed simultaneously with the priming or immediately subsequent to the priming, such that for rinsing a pressure difference is created between the extracorporeal circuit and the dialyzing liquid circuit and a liquid transfer is effected across the membrane of the dialyzer, in particular from the extracorporeal circuit to the dialyzing liquid circuit.

In other words, the present disclosure provides an extracorporeal blood treatment device which allows both the priming and the rinsing to be realized by supplying a liquid (priming/rinsing/dialyzing liquid) across the membrane of the dialyzer from the dialyzing liquid side. Thus, according to the disclosure no separate bag with saline solution/priming/rinsing liquid or, respectively, no substitute connection is needed on the machine for the priming and for the rinsing. Accordingly, the automatic priming and rinsing of the present disclosure is also applicable to extracorporeal blood treatment machines/dialysis machines which do not have a substitute connection/port. Furthermore, since no external saline bag is used, the automatic priming and rinsing according to the disclosure results in time savings for the nursing staff. Furthermore, the automatic priming and rinsing according to the disclosure enables that filling and rinsing (of) the dialyzer is possible without having to turn the dialyzer, so that this work step by the nursing staff is also eliminated. This is because, according to the disclosure, the dialyzer is preferably filled/filled up from below and any air bubbles potentially remaining in the dialyzer are preferably removed by the rinsing process/operation according to the disclosure.

To enable the automatic priming and rinsing according to the disclosure, the arterial section and the venous section of the extracorporeal circuit are short-circuited or, respectively, connected via a connector device.

The connector device is preferably an adapter into which both one end of the arterial section and one end of the venous section can be inserted, and thereby these can be fluidically connected. Since a Luer connection is preferably provided at both the end of the arterial section and the end of the venous section, the adapter is advantageously configured for connecting/joining two Luer connections. For example, the adapter available under the registered trademark COMBIFIX® of the applicant of the present patent application is a suitable connector device. However, the connector device according to the disclosure is not limited to this. In principle, any connector/any connector piece is conceivable, as long as it allows the arterial section of the extracorporeal circuit to be connected/short-circuited with/to the venous section of the extracorporeal blood circuit in a suitable manner.

The automatic priming and/or rinsing of the present disclosure is preferably implemented by a (suitable) control of the valve positions (OPEN/CLOSED) of the valves present/provided in the extracorporeal blood treatment device.

Further preferably, the automatic priming and/or rinsing of the present disclosure is (additionally also) realized by a (suitable) control of the flow pump, which is present/provided in the dialyzing liquid circuit.

According to the disclosure, both a dialyzer inlet valve and a dialyzer outlet valve are provided in the dialyzing liquid circuit. The dialyzer inlet valve is preferably provided/arranged at a dialyzing liquid inflow upstream of the dialyzer. The dialyzer outlet valve is preferably provided/arranged at a dialyzing liquid outflow downstream of the dialyzer.

Advantageously, a flow pump-inlet is provided/arranged in the dialyzing liquid inflow upstream of the dialyzer inlet valve. Further preferably, a flow pump-outlet is provided/arranged in the dialyzing liquid outflow downstream of the dialyzer outlet valve. According to the disclosure, however, also only one flow pump, i.e., either the flow pump-inlet or the flow pump-outlet, may be provided. The flow pump-inlet and/or the flow pump-outlet is/are preferably designed as gear pump/s. The at least one flow pump is preferably configured to supply priming/rinsing/dialyzing liquid from the dialyzing liquid circuit across the membrane of the dialyzer to the extracorporeal circuit.

The extracorporeal circuit preferably has at least one pressure sensor, which measures/monitors a pressure in the extracorporeal circuit and provides information about a pressure curve in the extracorporeal circuit to the control unit. The control unit of the present disclosure is preferably formed as a processor, in particular as a central computing or, respectively, processing unit (CPU). For example, the at least one pressure sensor is an arterial pressure sensor in the arterial section of the extracorporeal circuit upstream of a blood pump (preferably formed as roller pump to supply a fluid/a liquid by squeezing a tube), or a dialyzer inlet pressure sensor in the arterial section upstream of the dialyzer, or a venous pressure sensor in the venous section of the extracorporeal circuit. Preferably, all of the arterial pressure sensor and the dialyzer inlet pressure sensor and the venous pressure sensor are provided in the extracorporeal circuit.

Preferably, in the extracorporeal circuit at least one expansion chamber is provided, which is formed in particular as an air trap. For example, a venous expansion chamber or, respectively, a venous air trap is provided in the venous section of the extracorporeal circuit. Additionally or alternatively, an arterial expansion chamber or, respectively, an arterial air trap may be provided in the arterial section of the extracorporeal circuit.

The at least one pressure sensor, which may be provided in the extracorporeal circuit, can measure/acquire/monitor the pressure in the extracorporeal circuit at the at least one expansion chamber/air trap. For example, if a venous expansion chamber, or respectively, air trap is provided, venous pressure may be acquired/measured at the same via a venous pressure sensor. Alternatively or additionally, if an arterial expansion chamber or, respectively, air trap is provided, the arterial pressure or the dialyzer inlet pressure may be acquired/measured at the same via an arterial pressure sensor or a dialyzer inlet pressure sensor.

Downstream of the at least one pressure sensor (e.g. arterial pressure sensor, venous pressure sensor, dialyzer inlet pressure sensor), according to the disclosure preferably a level regulating pump is provided/arranged, which is formed in particular as an air compressor. In particular, the level regulating pump serves to adjust the level/gauge of the expansion chamber/air trap and can remove air from the tubing system/the extracorporeal circuit or push air into the tubing system/the extracorporeal circuit. For example, a venous expansion chamber/air trap may be provided at which the venous pressure is acquired via the venous pressure sensor, and the level regulating pump may be provided downstream of the venous pressure sensor.

According to the disclosure, the extracorporeal circuit has at least one vent valve. In other words, according to the disclosure somewhere (at any place/position) in the extracorporeal circuit at least one vent valve shall be provided, via which air can escape/be released from the extracorporeal circuit (via an opened valve).

Preferably, the at least one vent valve is provided at a section (tube section) of the extracorporeal circuit through which air can escape from a provided expansion chamber/air trap. For example, the vent valve may be arranged/provided downstream of a pressure sensor that measures/acquires the pressure at the expansion chamber/air trap, particularly preferably downstream of the level regulating pump.

According to a preferred embodiment of the present disclosure, preferably a venous expansion chamber/air trap is provided, at which the venous pressure is measured/acquired via a venous pressure sensor, and air can escape from the venous expansion chamber/air trap via a section (tube section) of the extracorporeal circuit, and the level regulating pump and the vent valve is provided/arranged in this section of the extracorporeal circuit. Alternatively or additionally, an arterial expansion chamber/air trap may also be provided, at which the pressure is measured/acquired via a pressure sensor, and air can escape from the arterial expansion chamber/air trap via a section (tube section) of the extracorporeal circuit, and the level regulating pump and the vent valve is provided/arranged in this section of the extracorporeal circuit.

According to the disclosure, the control unit of the extracorporeal blood treatment device is configured to control the priming such that a liquid, in particular priming/rinsing/dialyzing liquid, is supplied from the dialyzing liquid circuit across the membrane of the dialyzer to the extracorporeal blood circuit.

In an advantageous manner, the control unit is thereby configured, for the controlling of the priming, to open the dialyzer inlet valve and the at least one vent valve and to close the dialyzer outlet valve, and to control the at least one flow pump, in particular flow pump-inlet (upstream of the dialyzer in the dialyzing liquid circuit), so that it/this pumps the liquid, in particular priming/rinsing/dialyzing liquid, into the dialyzer at a required pressure. It is to be understood that if more than one vent valve is provided in the extracorporeal circuit, each vent valve is preferably opened such that air can escape via the vent valve or, respectively, vent valves during the priming/filling of the extracorporeal circuit with priming or, respectively, rinsing liquid.

The required pressure provided by the flow pump can be determined as a function of the dialyzer used, in particular as a function of the ultrafiltration coefficient and the volume of the dialyzer, and as a function of the extracorporeal circuit/tubing system used, in particular as a function of the volume of the extracorporeal circuit. In particular, the required pressure to be applied by the flow pump can be calculated as a function of the dialyzer used and the extracorporeal circuit/A/V tubing system used as follows (see equation 1 below)

$$\Delta p = \frac{V_{AV} + V_{dialyzer}}{\left(\frac{K_{UF}}{60 \text{ min}}\right)} \quad \text{(Equation 1)}$$

In other words, according to equation 1, in order to determine the required pressure $\Delta p$ to be applied by the flow pump, first the volumes of the extracorporeal circuit/tubing system $V_{AV}$ and of the dialyzer $V_{dialyzer}$ are added, and the sum is divided by an ultrafiltration coefficient, which indicates the ultrafiltration every minute in ml obtained per mmHg of transmembrane pressure (TMP). Thus, by the above equation 1, the pressure required from the dialyzing liquid side, which is provided by the flow pump, can be calculated, by means of which the extracorporeal circuit/tubing system and the dialyzer can be filled in one minute, that is, in other words, to prime/the priming takes one minute.

In order to let the entire volume stream/flow across the (hollow fiber) membrane of the dialyzer, advantageously the priming or, respectively, rinsing liquid is pressed through the membrane of the dialyzer not only from the dialyzing liquid side, but is also drawn on the side of the extracorporeal circuit in a suitable manner, in particular by creating a negative pressure or, respectively, depression in the extracorporeal circuit (for example by means of the blood pump or by means of the level regulating pump). Thereby, it has been found to be advantageous if the negative value of the pressure is used by means of which the priming or, respectively, rinsing liquid is pressed through the membrane of the dialyzer on the dialyzing liquid side.

In order to be able to perform the prime/priming according to the disclosure, the pressure in the extracorporeal circuit/tubing system can be reduced in an advantageous manner when the priming or, respectively, rinsing liquid is pressed or, respectively, drawn across the membrane of the dialyzer into the extracorporeal circuit/the extracorporeal tubing system. This is according to the disclosure enabled by the at least one vent valve, via which air can escape/flow out from the extracorporeal circuit.

According to a preferred embodiment, the prime/priming is performed in a time-controlled manner. In particular, (a) time-dependent priming/priming is conceivable, which is performed as a function of the used dialyzer (volume and $K_{UF}$), the used extracorporeal circuit (volume) and the applied pressure. Alternatively, the prime/priming may also be performed in a volume-controlled manner. In particular, it is thereby also conceivable to use the level regulating pump and to use it/this to measure the air volume during the venting. Preferably, the prime/priming may then be controlled so that it is terminated when the volume of the system is reached.

Preferably, the control unit is configured to, after completion of the priming and before the start of the rinsing, close the dialyzer inlet valve, to stop the at least one flow pump, in particular flow pump-inlet, to keep the at least one vent valve open, and to keep the dialyzer outlet valve closed.

The rinsing of the extracorporeal blood treatment device, in particular of the dialyzer and the extracorporeal circuit, is according to the disclosure controlled such that for the rinsing a pressure difference is created between the extracorporeal circuit and the dialyzing liquid circuit, for causing a transfer of the liquid across the membrane of the dialyzer from the extracorporeal circuit to the dialyzing liquid circuit.

Advantageously, the pressure difference between the extracorporeal circuit and the dialyzing liquid circuit is created by first building up/increasing the pressure in the extracorporeal circuit via a fluid flow/liquid flow of priming/rinsing/dialyzing liquid from the dialyzing liquid circuit across the membrane of the dialyzer into the extracorporeal circuit (with the (vent) valve(s) in the extracorporeal circuit closed), and by subsequently releasing/removing the pressure in the dialyzing liquid circuit (for example, by opening a valve, in particular the dialyzer outlet valve). This thus resulting pressure difference is then initially stored in the extracorporeal circuit, for example in an expansion chamber/balancing chamber/air trap. The stored pressure difference (excess pressure) in the extracorporeal circuit is according to the disclosure preferably reduced via a fluid flow from the extracorporeal circuit across the membrane of the dialyzer towards/back to the dialyzing liquid circuit. For this purpose, the valve, in particular the dialyzer outlet valve, is advantageously opened. The rinsing process according to the disclosure is thus, in other words, realized in particular by priming or, respectively, rinsing liquid initially flowing from the dialyzing liquid circuit into the extracorporeal circuit, and then flowing again from the extracorporeal circuit back into the dialyzing liquid circuit.

Overall, according to the disclosure, thus preferably the extracorporeal circuit/the AV tubing system is filled up to a maximum pressure in a first step. This is preferably followed by a pressure release by opening (of) the dialyzer outlet valve. As a result, the pressure in the extracorporeal circuit can also relax by the accumulated liquid preferably flowing back into the dialyzing liquid circuit and being drained via the dialyzer outlet valve. In other words, the volume stored in the expansion chamber/balancing chamber/air trap is reduced by pushing/pressing the liquid volume across the (hollow fiber) membrane of the dialyzer.

Advantageously, the rinsing process/the rinsing described above is performed several times or, respectively, repeated cyclically in order to remove ideally all residual substances/pyrogens present in the extracorporeal circuit and/or the dialyzer. Thereby, the duration of the entire rinsing process may preferably be set individually. The number of repetitions of the rinsing process/the rinsing depends in particular on the desired or, respectively, set or, respectively, required rinsing volume. For example, a minimum rinsing volume may be specified for an extracorporeal circuit/an A/V tubing system. For typical/commercially available extracorporeal circuits, it has been found in particular that preferably 5 to 30, particularly preferably 10 to 25, repetitions must be performed in order to perform the rinsing appropriately. In particular, thereby it has also been found that per rinsing process/operation approximately a rinsing volume of 20 ml to 40 ml, preferably 25 ml to 35 ml, particularly preferably 30 ml, is achieved. However, it goes without saying that the rinsing volume per rinsing process, as well as the number of repetitions, depend in particular on how much liquid can be additionally put into the extracorporeal circuit during pressure build-up. This means that the rinsing volume per rinsing process and the number of repetitions depend to a large extent on the extracorporeal circuit/A/V tubing system used, the dialyzer used, etc.

Preferably, the control unit is configured, for control(ling) (of) the rinsing: to create the pressure difference between the extracorporeal circuit and the dialyzing liquid circuit such that initially a predetermined maximum pressure of the liquid, in particular priming/rinsing/dialyzing liquid, is created in the dialyzing liquid circuit and the extracorporeal circuit via a pressure-generating means provided in the dialyzing liquid circuit, in particular the at least one flow pump, and then the predetermined maximum pressure is reduced in the dialyzing liquid circuit. In other words, preferably a pressure relaxation takes place in the dialyzing liquid circuit, for example by opening a valve (preferably the dialyzer outlet valve) provided in the dialyzing liquid circuit. Thereby, advantageously, the predetermined maximum pressure in the extracorporeal circuit is reduced via the liquid transfer from the extracorporeal circuit to the dialyzing liquid circuit across the membrane of the dialyzer.

The rinsing is according to the disclosure thus preferably realized by a stored pressure difference in the extracorporeal circuit and a control/driving/actuation of the valves (dialyzer inlet valve, dialyzer outlet valve, vent valve, etc.), pumps, etc. present in the extracorporeal blood treatment device. Thereby, especially the following control has proven to be advantageous:

Advantageously, the control unit is configured, for control (ling) (of) the rinsing: to open or to keep open the dialyzer inlet valve, to close or to keep closed the at least one vent valve, to close or to keep closed the dialyzer outlet valve; and to control the at least one flow pump such that it/this pumps the liquid, in particular priming/rinsing/dialyzing liquid, at a (predetermined) required pressure into the dialyzer, namely until a predetermined maximum pressure has been/is reached in the extracorporeal circuit.

Preferably, this prevents priming/rinsing/dialyzing liquid from escaping at the dialyzing liquid side during pressure build-up in the extracorporeal circuit. Furthermore, it is preferably avoided that priming/rinsing/dialyzing liquid or air can escape at the extracorporeal side. It is further advantageous if the same pressure (calculated according to equation 1) is created at the dialyzing liquid side by the flow pump as during the prime/priming.

The pressure build-up is preferably performed/carried out until a predetermined maximum pressure in the extracorporeal circuit is reached or, respectively, measured. For pressure measurement in the extracorporeal circuit, a (the at least one) pressure sensor may be used, for example the venous pressure sensor or the arterial pressure sensor or the dialyzer inlet pressure sensor. In particular, the predetermined maximum pressure depends on the dialyzer or on the components present in the extracorporeal circuit. For example, the specifications of the dialyzers used should be adhered to, in particular the maximum transmembrane pressure, which depends on the dialyzer type/the dialyzer used, and is generally also included in data sheets of dialyzers. Furthermore, the maximum pressure may be determined as a function of the components present in the extracorporeal circuit, for example such that a maximum volume of a provided/present balancing chamber/air trap is used for the determination of the maximum pressure. However, it is particularly preferred that the maximum pressure in the extracorporeal circuit is less than or equal to the maximum transmembrane pressure. Thereby, the general rule is that the extracorporeal circuit can be rinsed more quickly, which means that fewer repetitions of the rinsing process are required the higher the maximum transmembrane pressure (is). Preferably, the maximum pressure/excess pressure is less than 500 mmHg, particularly preferably less than 390 mmHg. However, according to the disclosure, also higher pressures are in principle possible or, respectively, conceivable.

Furthermore, it is advantageous if the control unit is configured, for the control(ling) (of) the rinsing, if the predetermined maximum pressure is present in the extracorporeal circuit, to close the dialyzer inlet valve, to stop the at least one flow pump, to keep the vent valve closed, and to open the dialyzer outlet valve. As a result, the pressure in the dialyzing liquid circuit is reduced or, respectively, removed, and the pressure difference between the extracorporeal circuit and the dialyzing liquid circuit (is) created. In other words, the pressure difference is then preferably stored as excess pressure in the extracorporeal circuit, and the predetermined maximum pressure/pressure difference or, respectively, excess pressure is then finally reduced in the extracorporeal circuit via the liquid transfer/fluid flow across the membrane of the dialyzer towards the dialyzing liquid circuit and towards the (opened) dialyzer outlet valve.

It is advantageous if at least two flow pumps are provided, wherein a second flow pump, in particular flow pump-outlet, supports the liquid transfer across the membrane of the dialyzer from the extracorporeal circuit to the dialyzing liquid circuit. In particular, if the second flow pump/flow pump-outlet provided downstream of the dialyzer operates occlusively/occludingly, it is imperative that the flow pump-outlet supports the liquid transfer. Otherwise it applies that the relaxation process may be supported by the second flow pump, but does not have to be supported.

Advantageously, the control unit is configured, for the control(ling) (of) the rinsing: if the predetermined maximum pressure in the extracorporeal circuit is reduced, to close the dialyzer outlet valve, if applicable, to stop the second flow pump/flow pump-outlet, and to again perform the entire rinsing process.

In summary, the control unit is thus preferably configured, for the control(ling) (of) the rinsing:
 a) to open or to keep open the dialyzer inlet valve, to close or to keep closed the at least one vent valve, to close or to keep closed the dialyzer outlet valve, and to control the at least one flow pump such that it/this pumps the liquid, in particular priming/rinsing/dialyzing liquid, at a required pressure into the dialyzer, namely until a predetermined maximum pressure is reached in the extracorporeal circuit;
 (b) if the predetermined maximum pressure is present in the extracorporeal circuit, to close the dialyzer inlet valve, to stop the at least one flow pump, to keep the vent valve closed, and to open the dialyzer outlet valve so that the predetermined maximum pressure in the extracorporeal circuit is reduced via liquid transfer across the membrane of the dialyzer towards the opened dialyzer outlet valve; and
 c) if/when the predetermined maximum pressure in the extracorporeal circuit is reduced, to close the dialyzer outlet valve, and to again perform the rinsing process starting from step a).

Preferably, the steps a) to c) are performed in chronological order by the control unit. Further preferably, the steps a) to c) are repeated cyclically so that the rinsing process according to the steps a) to c) is performed several times for appropriate rinsing of the dialyzer and the extracorporeal circuit.

Advantageously, a blood pump adapter/a pump segment of the blood tubing of the extracorporeal circuit is not inserted into a blood pump of the extracorporeal blood treatment device during the priming and rinsing. Thus, according to the disclosure, preferably no peristaltic pump is required during the priming and rinsing, and pyrogens/residuals are advantageously not dissolved when liquid is pumped with the peristaltic pump during the priming and rinsing.

In summary, an extracorporeal blood treatment device having an extracorporeal circuit, a dialyzer, and a dialyzing liquid circuit is provided, wherein the extracorporeal blood treatment device is prepared or, respectively, configured for the priming and rinsing thereof, and, for this purpose, an arterial section and a venous section of the extracorporeal circuit are connected via a connector device, and wherein a control unit of the extracorporeal blood treatment device is configured to control the priming such that a liquid is supplied from the dialyzing liquid circuit to the extracorporeal circuit via the dialyzer, and to control the rinsing such that it takes place via a created pressure difference between the extracorporeal circuit and the dialyzing liquid circuit, for effecting a liquid transfer across the dialyzer, in particular from the extracorporeal circuit to the dialyzing liquid circuit.

Further, the present disclosure relates to a method for priming and rinsing/flushing (of) an extracorporeal circuit and a dialyzer of an extracorporeal blood treatment device, particularly as described above, prior to a first-time use of the extracorporeal circuit and of the dialyzer, comprising the steps of: connecting or, respectively, short-circuiting of an arterial section and a venous section of the extracorporeal circuit of the extracorporeal blood treatment device; priming (of) the extracorporeal circuit and the dialyzer by supplying a liquid from a dialyzing liquid circuit of the extracorporeal blood treatment device to the extracorporeal circuit across a membrane of the dialyzer; and a rinsing of the extracorporeal circuit and the dialyzer to be performed simultaneously with the priming or immediately subsequent to the priming, comprising the steps: creating (of) a pressure difference between the extracorporeal circuit and the dialyzing liquid circuit; and rinsing (of) the extracorporeal circuit and the dialyzer via a liquid transfer across the membrane of the dialyzer, in particular from the extracorporeal circuit to the dialyzing liquid circuit.

Preferably, the rinsing comprises the following step: creating (of) the pressure difference between the extracorporeal circuit and the dialyzing liquid circuit such that initially a predetermined maximum pressure of the liquid, in particular priming/rinsing/dialyzing liquid, is created in the dialyzing liquid circuit and the extracorporeal circuit via a pressure-generating means provided in the dialyzing liquid circuit, in particular the at least one flow pump, and then the predetermined maximum pressure is reduced in the dialyzing liquid circuit.

Advantageously, the priming comprises the following steps: opening (of) a dialyzer inlet valve of the dialyzing liquid circuit and a vent valve of the extracorporeal circuit; closing (of) a dialyzer outlet valve of the dialyzing liquid circuit; and pumping (of) the liquid, in particular priming/rinsing/dialyzing liquid, at a required pressure into the dialyzer by means of a flow pump provided in the dialyzing liquid circuit.

Preferably, the rinsing comprises the following steps: opening or keeping open (of) the dialyzer inlet valve, closing or keeping closed (of) the vent valve, closing or keeping closed (of) the dialyzer outlet valve, and pumping (of) the liquid, in particular priming/rinsing/dialyzing liquid at a required pressure into the dialyzer, namely until a predetermined maximum pressure is reached in the extracorporeal circuit.

It is advantageous, if the rinsing further comprises the following step: if the predetermined maximum pressure is present in the extracorporeal circuit, closing (of) the dialyzer inlet valve, stopping (of) the at least one flow pump, keeping the vent valve closed, and opening (of) the dialyzer outlet valve, and therewith associated reducing (of) the predetermined maximum pressure in the extracorporeal circuit via the liquid transfer across the membrane of the dialyzer towards the opened dialyzer outlet valve.

Further preferably, the rinsing further comprises the following step: supporting (of) the liquid transfer across the membrane of the dialyzer from the extracorporeal circuit to the dialyzing liquid circuit using a flow pump.

In summary, the rinsing preferably comprises the following steps: (a) opening or keeping open (of) the dialyzer inlet valve, closing or keeping closed (of) the at least one vent valve, closing or keeping closed (of) the dialyzer outlet valve, and pumping (of) the liquid, in particular priming/rinsing/dialyzing liquid, at a required pressure into the dialyzer, namely until a predetermined maximum pressure is reached in the extracorporeal circuit; b) if the predetermined maximum pressure is present in the extracorporeal circuit, closing (of) the dialyzer inlet valve, stopping (of) the at least one flow pump, keeping the vent valve closed, and opening (of) the dialyzer outlet valve, and therewith associated reducing (of) the predetermined maximum pressure in the extracorporeal circuit via liquid transfer across the membrane of the dialyzer towards the opened dialyzer outlet valve; and c) if/when the predetermined maximum pressure in the extracorporeal circuit is reduced, closing (of) the dialyzer outlet valve, and again performing the rinsing process starting from step a).

The rinsing/the described rinsing process is thus preferably performed several times, in particular in a cyclically repeating manner.

In summary, the present disclosure provides fully automated priming and rinsing, wherein for the fully automated priming and rinsing no substitute port, no waste port, and no additional disposables/disposable items are required.

BRIEF DESCRIPTION OF THE DRAWINGS

The disclosure is further explained below with reference to figures.

DETAILED DESCRIPTION

The figures are of a schematic nature only and are intended solely for the understanding of the disclosure.

Figure 1:
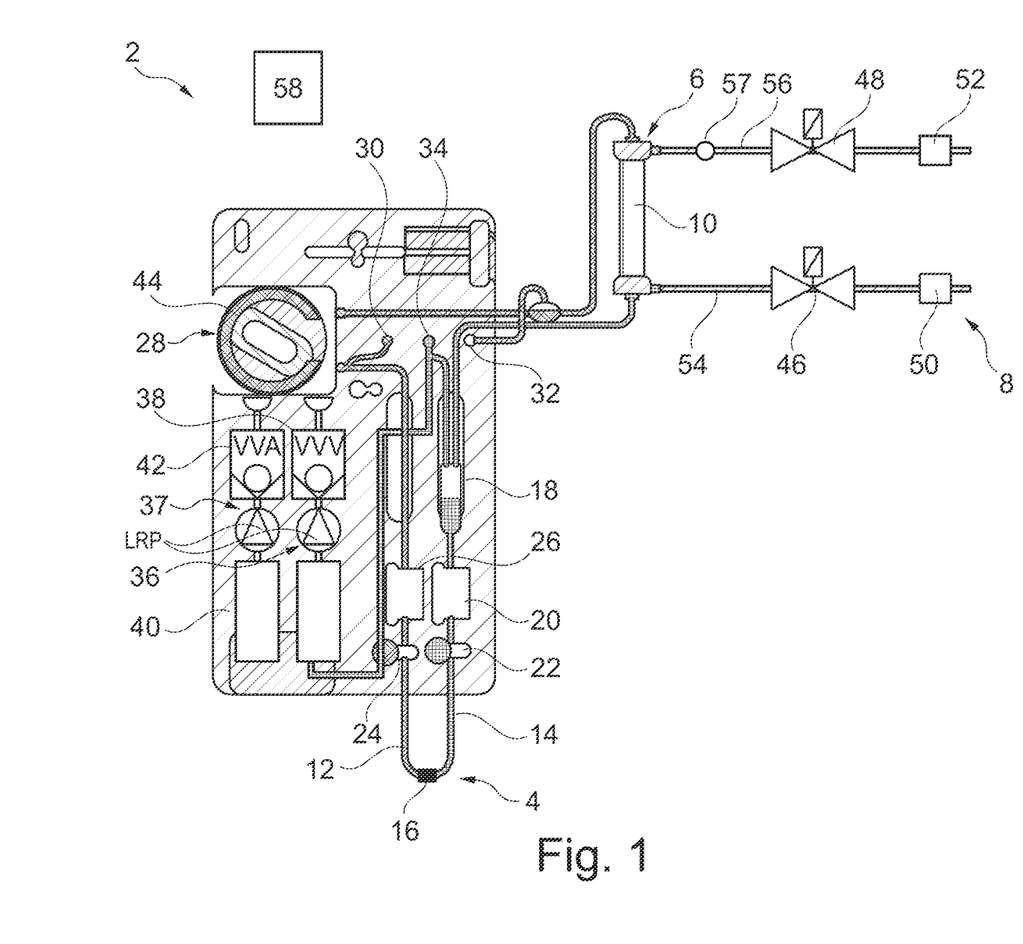
FIG. 1 shows an extracorporeal blood treatment device according to the present disclosure, with reference to which the automatic priming and rinsing according to the disclosure is explained.

FIG. 1 shows an extracorporeal blood treatment device (dialysis machine) 2. The extracorporeal blood treatment device 2 principally comprises an extracorporeal circuit (A/V tubing system) 4, a dialyzer 6, and a dialyzing liquid circuit 8. Thereby, the extracorporeal circuit 4 and the dialyzing liquid circuit 8 are separated from each other by a membrane 10 provided in the dialyzer 6.

The extracorporeal circuit 4 comprises an arterial section 12, which is located upstream of the dialyzer 6, and a venous section 14, which is located downstream of the dialyzer 6.

As can be seen from FIG. 1, the arterial section 12 and the venous section 14 are connected or, respectively, short-circuited via an adapter 16, which is an example of a connector device. In other words, both one end of the arterial section 12 and one end of the venous section 14 are inserted into the adapter 16 so that the arterial section 12 and the venous section 14 are fluidically connected to each other. Preferably, two Luer connectors, which are preferably provided at the ends of the arterial section 12 and the venous section 14, may be inserted into the adapter 16.

In the venous section 14 of the extracorporeal circuit 4, a venous expansion chamber or, respectively, air trap 18, a venous safety air detector 20, and a venous tube clamp 22 are arranged or, respectively, provided downstream of the dialyzer 6 (that is, starting from the dialyzer 6 in a direction towards the adapter 16).

In the arterial section 12, starting from the adapter 16 in a direction towards the dialyzer 6, an arterial tube clamp 24, an arterial safety air detector 26, and a blood pump 28 are provided.

In the arterial section 12, an arterial pressure upstream of or, respectively, before the blood pump 28 may be measured by an arterial pressure sensor 30. Furthermore, a dialyzer inlet pressure downstream of or, respectively, after the blood pump 28 and upstream or, respectively, before the dialyzer 6 (between the dialyzer 6 and the blood pump 28) may be measured by a dialyzer inlet pressure sensor 32. In the venous section 14, a venous pressure at/downstream of the venous expansion chamber or, respectively, air trap 18 may be measured by a venous pressure sensor 34. The pressure sensors 30, 32, 34 provided in the extracorporeal circuit 4 may measure/acquire/monitor the pressure at the respective locations in the extracorporeal circuit 4 at which they are arranged/provided.

As further shown in FIG. 1, the venous expansion chamber or, respectively, air trap 18 is connected to a level regulating pump 36. The level regulating pump 36 is used for an adjusting of the level of the venous expansion chamber or, respectively, air trap 18 and is formed, for example, as an air compressor. In particular, the level regulating pump 36 can remove air from the extracorporeal circuit 4 (in particular from the venous expansion chamber or, respectively, air trap 18) or press air into the extracorporeal circuit 4 (in particular into the venous expansion chamber or, respectively, air trap 18) such as to adjust the fluid level or, respectively, fluid gauge in the venous expansion chamber or, respectively, air trap 18.

Downstream of the level regulating pump 36A, a vent valve, in particular a venous vent valve 38, is provided, through which air can escape from the extracorporeal circuit/tubing system 4. In FIG. 1, the venous expansion chamber/air trap 18 is thus also connected to the vent valve 38, so that air can principally escape from the venous expansion chamber/air trap 18 or, respectively, from the extracorporeal circuit 4 when/if the vent valve 38 is open.

As further shown in FIG. 1, a further or, respectively, second level regulating pump 37 may be provided at a machine front 40 of the extracorporeal blood treatment device 2. For example, the further or, respectively, second level regulating pump 37 could be connected to an arterial expansion chamber or, respectively, air trap (not provided in FIG. 1), so that in principle a fluid level or, respectively, a fluid gauge of an arterial expansion chamber or, respectively, air trap could be adjustable via the second level regulating pump 37. Downstream of this second level regulating pump 37, in FIG. 1 a further or, respectively, second vent valve, in particular an arterial vent valve 42, is arranged, via which air could escape from an arterial expansion chamber/air trap and thus from the extracorporeal circuit 4.

In principle, however, it is also conceivable that even if both a venous expansion chamber/air trap 18 and an arterial expansion chamber/air trap are provided, only one single level regulating pump is provided, and this can adjust—for example via an intermediate valve—the fluid levels or, respectively, fluid gauges of both air traps. In this case, only one vent valve could be provided downstream of the one level regulating pump.

As can be seen in FIG. 1, the extracorporeal circuit 4 (in particular a blood pump adapter 44 thereof) is already inserted into the blood pump 28, which is preferably formed as a roller pump or, respectively, peristaltic pump and is configured to supply a fluid/a liquid by squeezing a tube. However, according to the present disclosure, it is preferred that the blood pump adapter 44 of the extracorporeal circuit 4 is not yet inserted into the blood pump 28 during the priming and rinsing, since the blood pump 28 is not necessarily required for the automatic priming and rinsing according to the disclosure. When the blood pump adapter 44 is not yet inserted into the blood pump 28 during the priming and rinsing, the priming and rinsing are greatly simplified. In particular, in this case, the blood pump adapter (tube) 44 is not occluded or, respectively, squeezed by the (usually occludingly operating) blood pump 28, and a control of the blood pump 28 is not required neither during the priming nor during the rinsing.

The dialyzing liquid circuit 8 comprises a dialyzer inlet valve 46, a dialyzer outlet valve 48, a flow pump-inlet 50 and a flow pump-outlet 52. However, it is generally sufficient if only one flow pump, for example the flow pump-inlet 50, is provided in the dialyzing liquid circuit 8. The dialyzer inlet valve 46 and the flow pump-inlet 50 are thereby provided/arranged at a dialyzing liquid inflow 54 upstream of the dialyzer 6. The dialyzer outlet valve 48 and the flow pump-outlet 52 are provided/arranged at a dialyzing liquid outflow 56 downstream of the dialyzer 6. The flow pump-inlet 50 and the flow pump-outlet 52 are preferably gear pumps. A pressure sensor 57 is provided in the dialyzing liquid outflow 56 in FIG. 1. In principle, however, according to the disclosure the pressure sensor 57 may also be arranged in the dialyzing liquid inflow 54. It is also conceivable that several pressure sensors, for example two or three, are provided in the dialyzing liquid circuit 8. However, at least one pressure sensor 57 should be provided in the dialyzing liquid circuit 8 so that (together with the pressure sensor/pressure sensors provided in the extracorporeal circuit 4, for example arterial pressure sensor 30, dialyzer inlet pressure sensor 32, venous pressure sensor 34) the transmembrane pressure can be determined.

The extracorporeal blood treatment device 2 further has a control unit 58, which is preferably formed as a processor, in particular as a central computing or, respectively, processing unit (CPU). The control unit 58 receives information from sensors which are provided in the extracorporeal blood treatment device 2. Thereby, merely as examples the sensors shown in FIG. 1 are to mention, i.e. the arterial pressure sensor 30, the dialyzer inlet pressure sensor 32, the venous pressure sensor 34, or the pressure sensor 57 in the dialyzing liquid circuit 8. On the other hand, the control unit 58 controls or, respectively, actuates actuators which are provided in the extracorporeal blood treatment device 2. Thereby, merely as examples the valves or pumps shown in FIG. 1, i.e. in particular the vent valves 38 and 42, the dialyzer inlet valve 46, the dialyzer outlet valve 48, the flow pump-inlet 50, the flow pump-outlet 52, the blood pump 28, the level regulating pumps 36, 37, etc., are to mention.

The control unit 58 controls an automatic priming. In particular, it controls the priming such that the liquid (priming/rinsing/or, respectively, dialyzing liquid) is supplied from the dialyzing liquid circuit 8 across the membrane 10 of the dialyzer 6 to the extracorporeal circuit 4. Thereby, the control unit 58 initially opens the dialyzer inlet valve 46 and the (venous) vent valve (VVV) 38. If the (arterial) vent valve (VVA) 42 were connected to the extracorporeal circuit 4, in particular to the arterial section 12 of the extracorporeal circuit 4, the control unit 58 would open also the (arterial) vent valve 42. Further, the control unit 58 closes the dialyzer outlet valve 48. In this condition, the control unit 58 controls the flow pump-inlet 50 to pump the liquid (priming/rinsing/ or, respectively, dialyzing liquid) into the dialyzer 6 at a required pressure.

The control unit 58 is preferably configured to calculate the required pressure itself and sets a parameter of the flow pump-inlet, for example the flow rate/the volume flow, accordingly. The control unit 58 obtains the information required for the calculation (see equation 1 above), in particular the volumes of the dialyzer 6 and the extracorporeal circuit 4, as well as the ultrafiltration coefficient $K_{UF}$, for example, via a manual input (such as via a user interface not shown) of the tubing system/extracorporeal circuit 4 used and the dialyzer 6 used. Alternatively, the tubing system 4 used and the dialyzer 6 used may also be read in, for example, via a reader not shown, and the information read in may be transmitted to the control unit 58.

Preferably, the liquid (priming/rinsing/or, respectively, dialyzing liquid) is not only "pushed" through the membrane 10 of the dialyzer 6 via the flow pump-inlet 50, but on one side of the extracorporeal circuit 4 the liquid is also "drawn" through the membrane 10 of the dialyzer 6 by generating a depression (negative pressure). This depression/negative pressure may be created, for example, by means of the level regulating pump 36.

During the priming, the dialyzer 6 and the extracorporeal circuit 4 are filled with the liquid (priming/rinsing/or, respectively, dialyzing liquid). A control of the priming from the control unit 58 may be time-controlled or volume-controlled. For example, the control unit 58 may calculate in advance a time required for the priming, and stop the priming process when this calculated required time has elapsed. Alternatively, the air volume leaving the extracorporeal circuit 4 may be measured by means of the level regulating pump 36, and the corresponding information may be transmitted to the control unit 58, and the control unit 58 terminates the priming process when/if the volume of air of the dialyzer 6 and the extracorporeal circuit 4 is reached.

Figure 2:
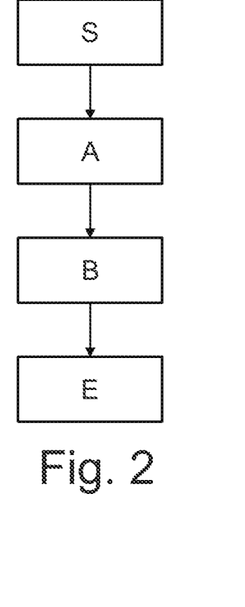
FIG. 2 shows a flow diagram of the automatic priming according to the disclosure.

The automatic priming according to the disclosure can be summarized in its simplest implementation according to the flow diagram shown in FIG. 2, as follows: The automatic priming is started at "S" for "Start". At A, the dialyzer inlet valve 46 and the at least one vent valve 38 are opened or remain opened, and the dialyzer outlet valve 48 is closed or remains closed. At B, the flow pump-inlet 50 is controlled so that it/this pumps the priming/rinsing/dialyzing liquid into the dialyzer 6 at a required pressure. If a termination criterion is met (time control or volume control), the automatic priming is terminated at "E" for "End".

The control unit 58 also controls an automatic rinsing of the dialyzer 6 and the extracorporeal circuit 4. Preferably, the rinsing takes place immediately subsequent to the priming. If/when the priming is completed/finished, that is, when the dialyzer 6 and extracorporeal circuit 4 are filled (up) with the liquid (priming/rinsing/or, respectively, dialyzing liquid), the control unit 58 closes the dialyzer inlet valve 46 and stops the flow pump-inlet 50. The vent valve 38 (or, respectively, the vent valves 38 and 42) initially remains opened and the dialyzer outlet valve 48 remains closed. To begin the rinsing, the control unit 58 opens the dialyzer inlet valve 46 and closes the vent valve 38 (or, respectively, the vent valves 38 and 42). The dialyzer outlet valve 48 remains closed. In this state, the control unit 58 controls the flow pump-inlet 50 so that it/this pumps liquid into the dialyzer 6 at a required pressure. In other words, the flow pump-inlet 50 generates an excess pressure. This results initially in a pressure increase in the dialyzing liquid circuit 8, which is transferred to the extracorporeal circuit 4 by the liquid passing across the membrane 10 (pressure balance). This process is continued until the target pressure (desired excess pressure/predetermined maximum pressure) is reached in the extracorporeal circuit 4.

The predetermined maximum pressure in the extracorporeal circuit 4 may be reached, for example, when the maximum transmembrane pressure of the dialyzer 6 used is reached, or when the maximum level/the maximum fluid volume of the venous expansion chamber/air trap 18 is reached.

When/if the predetermined maximum pressure is present in the extracorporeal circuit 4, the control unit 58 closes the dialyzer inlet valve 46, stops the flow pump-inlet 50, and opens the dialyzer outlet valve 48. This achieves that the pressure on the dialyzing liquid side/in the dialyzing liquid circuit 8 can relax. A pressure difference between the extracorporeal circuit 4 and the dialyzing liquid circuit 8 is thus created. This has the effect that the excess pressure or, respectively, pressure difference stored in the extracorporeal circuit 4 is released or, respectively, reduced via a fluid flow across the membrane 10 of the dialyzer 6 from the extracorporeal circuit 4 to the dialyzing liquid circuit 8 towards the opened dialyzer outlet valve 48. This process may optionally be supported by the flow pump-outlet 52.

In other words, according to the disclosure, the automatic rinsing is realized, by means of suitable valve/and pump actuations, by initially creating a fluid flow from the dialyzing liquid circuit 8 via the dialyzer 6 to the extracorporeal circuit 4, and then a fluid flow from the extracorporeal circuit 4 via the dialyzer 6 to the dialyzing liquid circuit 8. The fluid flow according to the disclosure is generated by initially creating a maximum pressure in the extracorporeal circuit 4 (fluid flow in the one direction), then reducing the pressure in the dialyzing liquid circuit 8 so that the pressure difference between the extracorporeal circuit 4 and the dialyzing liquid circuit 8 is created, and finally reducing the pressure difference/excess pressure stored in the extracorporeal circuit 4 via a fluid flow in the other direction (back).

After a pressure relaxation has occurred in the extracorporeal circuit 4, the control unit 58 closes the dialyzer outlet valve 48 and the described rinsing process is repeated (several times), namely until the required rinsing volume is reached.

Figure 3:
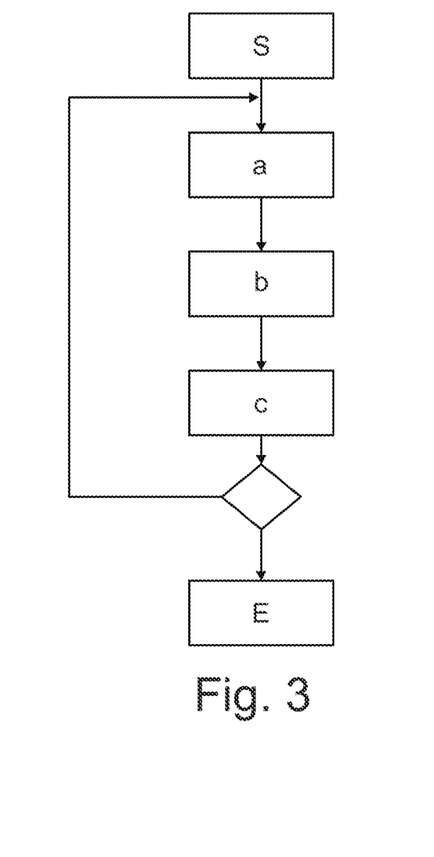
FIG. 3 shows a flow diagram of the automatic rinsing according to the disclosure.

The automatic rinsing according to the disclosure can altogether be summarized in its simplest implementation according to the flow diagram shown in FIG. 3, as follows: The automatic rinsing is started at "S" for "Start". At a, the dialyzer inlet valve 46 is opened or remains opened, the at least one vent valve 38 is closed or remains closed, the dialyzer outlet valve 48 is closed or remains closed, and the flow pump-inlet 50 is controlled that it/this pumps the priming/rinsing/dialyzing liquid into the dialyzer 6 at a required pressure, namely until a predetermined maximum pressure is reached in the extracorporeal circuit 4. At b, if/when the predetermined maximum pressure is present in the extracorporeal circuit 4, the dialyzer inlet valve 46 is closed, the flow pump-inlet 50 is stopped, the vent valve 38 is kept closed, and the dialyzer outlet valve 48 is opened so that the predetermined maximum pressure in the extracorporeal circuit 4 is reduced via the liquid transfer across the membrane 10 of the dialyzer 6 towards the opened dialyzer outlet valve 48. At c, if/when the predetermined maximum pressure in the extracorporeal circuit 4 is reduced, the dialyzer outlet valve 48 is closed. Subsequently, it is checked if the required rinsing volume has already been reached. If this is not the case, the rinsing process, i.e. steps a, b and c, is performed again. If the required rinsing volume has been reached, the automatic rinsing is ended at "E" for "End".

The invention claimed is:

1. An extracorporeal blood treatment device comprising:
an extracorporeal circuit comprising an arterial section and a venous section;
a dialyzer; and
a dialyzing liquid circuit, wherein:
the extracorporeal circuit and the dialyzing liquid circuit are separated from each other by a membrane provided in the dialyzer,
the extracorporeal blood treatment device is prepared or, respectively, configured for priming and rinsing of the extracorporeal circuit and the dialyzer prior to a first-time use of the extracorporeal circuit and the dialyzer, and for this purpose the arterial section and the venous section are short-circuited or, respectively, connected via a connector device,
the dialyzing liquid circuit has a dialyzer inlet valve, a dialyzer outlet valve and at least one flow pump,
the extracorporeal circuit has at least one vent valve,
the extracorporeal blood treatment device further comprises a control unit, which is configured to control priming such that a liquid is supplied from the dialyzing liquid circuit across the membrane of the dialyzer to the extracorporeal circuit,
the control unit is further configured to control rinsing of the extracorporeal blood treatment device to be performed simultaneously with priming or immediately subsequent to priming such that a pressure difference for rinsing is created between the extracorporeal circuit and the dialyzing liquid circuit, and a liquid transfer is effected across the membrane from the extracorporeal circuit to the dialyzing liquid circuit, and
the control unit is configured, for controlling priming:
to open or keep open the dialyzer inlet valve and the at least one vent valve, and to close or to keep closed the dialyzer outlet valve, and
to control the at least one flow pump so that the at least one flow pump pumps the liquid into the dialyzer at a required pressure.

2. The extracorporeal blood treatment device according to claim 1, wherein the control unit is configured, for controlling rinsing, to create the pressure difference such that initially a predetermined maximum pressure of the liquid is created in the dialyzing liquid circuit and the extracorporeal circuit via a pressure-generating means provided in the dialyzing liquid circuit, and then the predetermined maximum pressure is reduced in the dialyzing liquid circuit.

3. The extracorporeal blood treatment device according to claim 1, wherein the control unit is configured, for controlling of the rinsing:
to open or to keep open the dialyzer inlet valve,
to close or to keep closed the at least one vent valve,
to close or to keep closed the dialyzer outlet valve, and
to control the at least one flow pump so that the at least one flow pump pumps the liquid at a required pressure into the dialyzer until a predetermined maximum pressure is reached in the extracorporeal circuit.

4. The extracorporeal blood treatment device according to claim 3, wherein the control unit is configured, for controlling rinsing:
when the predetermined maximum pressure is present in the extracorporeal circuit, to close the dialyzer inlet valve, to stop the at least one flow pump, to keep the vent valve closed, and to open the dialyzer outlet valve so that the predetermined maximum pressure in the extracorporeal circuit is reduced via the liquid transfer across the membrane of the dialyzer towards the opened dialyzer outlet valve.

5. The extracorporeal blood treatment device according to claim 4, wherein the at least one flow pump comprises a first flow pump and a second flow pump, and wherein the second flow pump supports the liquid transfer across the membrane of the dialyzer from the extracorporeal circuit to the dialyzing liquid circuit.

6. A method for priming and rinsing of an extracorporeal circuit and of a dialyzer of an extracorporeal blood treatment device prior to a first-time use of the extracorporeal circuit and of the dialyzer, the method comprising the steps of:
   connecting or, respectively, short-circuiting an arterial section and a venous section of the extracorporeal circuit of the extracorporeal blood treatment device; and
   priming the extracorporeal circuit and the dialyzer by supplying a liquid from a dialyzing liquid circuit of the extracorporeal blood treatment device to the extracorporeal circuit across a membrane of the dialyzer,
   wherein the step of priming the extracorporeal circuit and the dialyzer comprises the steps of:
   opening or keeping open a dialyzer inlet valve of the dialyzing liquid circuit and a vent valve of the extracorporeal circuit;
   closing or keeping closed a dialyzer outlet valve of the dialyzing liquid circuit; and
   pumping the liquid at a required pressure into the dialyzer with a flow pump provided in the dialyzing liquid circuit,
   the method further comprising the step of:
   rinsing of the extracorporeal circuit and the dialyzer simultaneously with priming or immediately subsequent to priming, wherein rinsing comprises the steps of:
   creating a pressure difference between the extracorporeal circuit and the dialyzing liquid circuit; and
   rinsing the extracorporeal circuit and the dialyzer via a liquid transfer across the membrane of the dialyzer from the extracorporeal circuit to the dialyzing liquid circuit.

7. The method for priming and rinsing of an extracorporeal blood treatment device according to claim 6, wherein the step of rinsing comprises:
   creating the pressure difference between the extracorporeal circuit and the dialyzing liquid circuit such that initially a predetermined maximum pressure of the liquid is created in the dialyzing liquid circuit and the extracorporeal circuit via a pressure-generating means provided in the dialyzing liquid circuit, and then the predetermined maximum pressure is reduced in the dialyzing liquid circuit.

8. The method for priming and rinsing of an extracorporeal blood treatment device according to claim 7, wherein the step of rinsing further comprises the steps of:
   opening or keeping open of the dialyzer inlet valve;
   closing or keeping closed of the vent valve;
   closing or keeping closed of the dialyzer outlet valve; and
   pumping of the liquid, in particular priming/rinsing/dialyzing liquid at a required pressure into the dialyzer until a predetermined maximum pressure is reached in the extracorporeal circuit.

9. The method for priming and rinsing of an extracorporeal blood treatment device according to claim 8, wherein the rinsing further comprises the step of:
   when the predetermined maximum pressure is present in the extracorporeal circuit, closing of the dialyzer inlet valve, stopping of the at least one flow pump, keeping the vent valve closed, and opening of the dialyzer outlet valve, and therewith associated reducing of the predetermined maximum pressure in the extracorporeal circuit via the liquid transfer across the membrane of the dialyzer towards the opened dialyzer outlet valve.

10. The method for priming and rinsing of an extracorporeal blood treatment device according to claim 9, wherein rinsing further comprises the step of supporting the liquid transfer across the membrane of the dialyzer from the extracorporeal circuit to the dialyzing liquid circuit with a flow pump.

11. An extracorporeal blood treatment device comprising:
    an extracorporeal circuit comprising an arterial section and a venous section, a dialyzer and a dialyzing liquid circuit, wherein:
    the extracorporeal circuit and the dialyzing liquid circuit are separated from each other by a membrane provided in the dialyzer,
    the extracorporeal blood treatment device is prepared or, respectively, configured for priming and rinsing of the extracorporeal circuit and the dialyzer prior to a first-time use of the extracorporeal circuit and the dialyzer, and for this purpose the arterial section and the venous section are short-circuited or, respectively, connected via a connector device,
    the dialyzing liquid circuit has a dialyzer inlet valve, a dialyzer outlet valve and at least one flow pump,
    the extracorporeal circuit has at least one vent valve,
    the extracorporeal blood treatment device has a control unit, which is configured to control priming such that a liquid is supplied from the dialyzing liquid circuit across the membrane of the dialyzer to the extracorporeal circuit,
    the control unit is configured to control rinsing of the extracorporeal blood treatment device simultaneously with priming or immediately subsequent to priming such that for rinsing a pressure difference is created between the extracorporeal circuit and the dialyzing liquid circuit and a liquid transfer is effected across the membrane of the dialyzer from the extracorporeal circuit to the dialyzing liquid circuit, and
    the control unit is configured, for controlling of the rinsing:
    to open or to keep open the dialyzer inlet valve,
    to close or to keep closed the at least one vent valve,
    to close or to keep closed the dialyzer outlet valve, and
    to control the at least one flow pump so that it pumps the liquid at a required pressure into the dialyzer, namely until a predetermined maximum pressure is reached in the extracorporeal circuit.

12. A method for priming and rinsing of an extracorporeal circuit and of a dialyzer of an extracorporeal blood treatment device prior to a first-time use of the extracorporeal circuit and of the dialyzer, the method comprising the steps of:
    connecting or, respectively, short-circuiting an arterial section and a venous section of the extracorporeal circuit of the extracorporeal blood treatment device;
    priming the extracorporeal circuit and the dialyzer by supplying a liquid from a dialyzing liquid circuit of the extracorporeal blood treatment device to the extracorporeal circuit across a membrane of the dialyzer; and
    rinsing the extracorporeal circuit and the dialyzer simultaneously with priming or immediately subsequent to priming, wherein the step of rinsing the extracorporeal circuit and the dialyzer comprises the steps of:

creating a pressure difference between the extracorporeal circuit and the dialyzing liquid circuit;
rinsing the extracorporeal circuit and the dialyzer via a liquid transfer across the membrane of the dialyzer from the extracorporeal circuit to the dialyzing liquid circuit;
opening or keeping open the dialyzer inlet valve;
closing or keeping closed the vent valve;
closing or keeping closed the dialyzer outlet valve, and
pumping the liquid at a required pressure into the dialyzer until a predetermined maximum pressure is reached in the extracorporeal circuit.

\* \* \* \* \*